United States Patent
Aber et al.

(10) Patent No.: US 9,496,924 B2
(45) Date of Patent: Nov. 15, 2016

(54) MOBILE WIRELESS POWER SYSTEM

(71) Applicant: EVERHEART SYSTEMS INC., Webster, TX (US)

(72) Inventors: Greg S. Aber, Houston, TX (US); Christopher G. DuPont, League City, TX (US)

(73) Assignee: EverHeart Systems, Inc., Webster, TX (US)

( * ) Notice: Subject to any disclaimer, the term of this patent is extended or adjusted under 35 U.S.C. 154(b) by 589 days.

(21) Appl. No.: 13/842,041

(22) Filed: Mar. 15, 2013

(65) Prior Publication Data
US 2013/0241306 A1  Sep. 19, 2013

Related U.S. Application Data

(63) Continuation-in-part of application No. 13/038,671, filed on Mar. 2, 2011, now Pat. No. 8,901,775.
(Continued)

(51) Int. Cl.
*H04B 5/00* (2006.01)
*H01Q 1/27* (2006.01)
(Continued)

(52) U.S. Cl.
CPC ......... *H04B 5/0037* (2013.01); *A61N 1/3787* (2013.01); *H01Q 1/273* (2013.01);
(Continued)

(58) Field of Classification Search
None
See application file for complete search history.

(56) References Cited

U.S. PATENT DOCUMENTS 5,290,227 A  3/1994  Pasque
5,370,509 A  12/1994  Golding et al.
(Continued)

FOREIGN PATENT DOCUMENTS

CA  2209179 A1  7/1996
EP  1113177 A2  7/2001
(Continued)

OTHER PUBLICATIONS

Dixon, L.H., "Eddy Current Losses in Transformer Windings and Circuit Wiring," http://focus.ti.com/lit/ml/slup197/slup197.pdf>.
(Continued)

*Primary Examiner* — Jared Fureman
*Assistant Examiner* — Aqeel Bukhari
(74) *Attorney, Agent, or Firm* — Nathan S. Smith; Mark I. Bentley; McDermott Will & Emery LLP

(57) ABSTRACT

A mobile wireless power system capable of transmitting power through the skin to energize an implanted medical device without percutaneous wires and without precise positioning includes an external mobile wireless power source and an implantable receiving assembly. The mobile wireless power source is wearable by the patient and includes an excitation coil and transmitting resonant coil which are inductively coupled to each other and are housed in a durable housing. The implantable receiving assembly includes a receiving resonant coil and a power pick-up coil which are also inductively coupled to each other. The transmitting and receiving resonant coils are constructed as to have closely matched or identical resonant frequencies so that the magnetic field produced by the transmitting resonant coil is able to cause the receiving resonant coil to resonate strongly.

14 Claims, 12 Drawing Sheets

Related U.S. Application Data

(60) Provisional application No. 61/421,779, filed on Dec. 10, 2010.

(51) Int. Cl.

| | | |
|---|---|---|
| *H01Q 7/00* | (2006.01) | |
| *H02J 7/02* | (2016.01) | |
| *H02J 5/00* | (2016.01) | |
| *H02J 7/00* | (2006.01) | |
| *H02J 7/04* | (2006.01) | |
| *A61N 1/378* | (2006.01) | |
| *A61N 1/39* | (2006.01) | |
| *A61N 1/36* | (2006.01) | |
| *A61N 1/362* | (2006.01) | |

(52) U.S. Cl.
CPC ............... *H01Q 7/00* (2013.01); *H02J 5/005* (2013.01); *H02J 7/0047* (2013.01); *H02J 7/0054* (2013.01); *H02J 7/025* (2013.01); *H02J 7/045* (2013.01); *H04B 5/0093* (2013.01); *A61N 1/362* (2013.01); *A61N 1/3605* (2013.01); *A61N 1/3956* (2013.01); *H02J 2007/0096* (2013.01); *H04B 5/0075* (2013.01)

(56) References Cited

U.S. PATENT DOCUMENTS

| | | | |
|---|---|---|---|
| 5,702,431 A | 12/1997 | Wang et al. | |
| 6,048,363 A | 4/2000 | Nagyszalanczy et al. | |
| 6,227,797 B1 | 5/2001 | Watterson et al. | |
| 6,234,772 B1 | 5/2001 | Wampler et al. | |
| 6,240,318 B1 | 5/2001 | Phillips | |
| 6,445,956 B1 | 9/2002 | Laird et al. | |
| 6,547,530 B2 | 4/2003 | Ozaki et al. | |
| 6,593,841 B1 | 7/2003 | Mizoguchi et al. | |
| 6,894,456 B2 | 5/2005 | Tsukamoto et al. | |
| 7,616,997 B2 | 11/2009 | Kieval et al. | |
| 7,682,301 B2 | 3/2010 | Wampler et al. | |
| 7,699,586 B2 | 4/2010 | LaRose et al. | |
| 7,741,734 B2 | 6/2010 | Joannopoulos | |
| 7,825,543 B2 | 11/2010 | Karalis et al. | |
| 8,362,651 B2 | 1/2013 | Hamam et al. | |
| 8,551,163 B2 | 10/2013 | Aber et al. | |
| 8,901,775 B2 | 12/2014 | Armstrong et al. | |
| 2003/0091249 A1 | 5/2003 | Kurimura et al. | |
| 2006/0155159 A1 | 7/2006 | Melvin | |
| 2008/0211320 A1 | 9/2008 | Cook et al. | |
| 2008/0269828 A1 | 10/2008 | Sequeira Abreu | |
| 2009/0051224 A1 | 2/2009 | Cook et al. | |
| 2009/0058189 A1 | 3/2009 | Cook et al. | |
| 2009/0058361 A1 | 3/2009 | John | |
| 2009/0072628 A1 | 3/2009 | Cook et al. | |
| 2009/0079268 A1 | 3/2009 | Cook et al. | |
| 2009/0112626 A1 | 4/2009 | Talbot et al. | |
| 2009/0224609 A1 | 9/2009 | Cook et al. | |
| 2009/0234447 A1 | 9/2009 | LaRose et al. | |
| 2009/0270679 A1 | 10/2009 | Hoeg et al. | |
| 2010/0045114 A1 | 2/2010 | Sample et al. | |
| 2010/0052811 A1 | 3/2010 | Smith et al. | |
| 2010/0063347 A1 | 3/2010 | Yomtov et al. | |
| 2010/0102640 A1 | 4/2010 | Joannopoulos et al. | |
| 2010/0102641 A1 | 4/2010 | Joannopoulos et al. | |
| 2010/0109445 A1 | 5/2010 | Kurs et al. | |
| 2010/0117456 A1 | 5/2010 | Karalis et al. | |
| 2010/0133920 A1 | 6/2010 | Joannopoulos et al. | |
| 2010/0164296 A1 | 7/2010 | Kurs et al. | |
| 2010/0184371 A1 | 7/2010 | Cook et al. | |
| 2010/0185280 A1 | 7/2010 | Ayre et al. | |
| 2010/0210233 A1 | 8/2010 | Cook et al. | |
| 2010/0219694 A1 | 9/2010 | Kurs et al. | |
| 2010/0231053 A1 | 9/2010 | Karalis et al. | |
| 2010/0259108 A1 | 10/2010 | Giler et al. | |
| 2010/0277005 A1 | 11/2010 | Karalis et al. | |
| 2010/0305662 A1 | 12/2010 | Ozawa et al. | |
| 2010/0327661 A1 | 12/2010 | Karalis et al. | |
| 2011/0195666 A1 | 8/2011 | Forsell | |
| 2011/0281535 A1 | 11/2011 | Low et al. | |
| 2012/0010079 A1 | 1/2012 | Sedwick | |
| 2012/0032522 A1 | 2/2012 | Schatz et al. | |
| 2012/0089225 A1 | 4/2012 | Akkerman et al. | |
| 2012/0112554 A1 | 5/2012 | Kim et al. | |
| 2012/0119587 A1 | 5/2012 | Cheon et al. | |
| 2012/0139355 A1 | 6/2012 | Ganem et al. | |
| 2012/0146575 A1 | 6/2012 | Armstrong et al. | |
| 2012/0150291 A1 | 6/2012 | Aber et al. | |
| 2012/0153893 A1 | 6/2012 | Schatz et al. | |
| 2013/0345493 A1 | 12/2013 | Aber et al. | |
| 2014/0252873 A1* | 9/2014 | Irish | H03F 1/523 307/104 |
| 2014/0255225 A1 | 9/2014 | Aber et al. | |
| 2015/0061591 A1 | 3/2015 | Armstrong et al. | |

FOREIGN PATENT DOCUMENTS

| | | |
|---|---|---|
| WO | WO-2009/091267 A2 | 7/2009 |
| WO | WO-2010/042054 A1 | 4/2010 |

OTHER PUBLICATIONS

Murgatroyd, et al., "The Frequency Dependence of Resistance in Foilwound Inductors," Electrocomponent Science and Technology 1979, vol. 5, pp. 219-222.

Sample, et al., "Analysis, Experimental Results, and Range Adaptation of Magnetically Coupled Resonators for Wireless Power Transfer," IEEE, 2010.

Kurs, A., "Power Transfer Through Strongly Coupled Resonances," MIT Department of Physics, Master's Thesis, Sep. 2007.

\* cited by examiner

MOBILE WIRELESS POWER SYSTEM

FIELD

This invention relates to powering devices with wireless energy transfer.

BACKGROUND

Many medical devices require electrical power to operate. Non-limiting examples of such medical devices may include pacemakers, defibrillators, drug infusion pumps, neural stimulators, ventricular assist devices (VAD), and total artificial hearts (TAH). Some devices, such as pacemakers and drug infusion pumps, require such little power that an implanted non-rechargeable battery can last for several years, reducing the need for an implantable rechargeable power source. Other devices, such as some neural stimulators, may require power levels that an implanted non-rechargeable battery cannot supply for more than a few days or weeks. These devices require the use of an implantable rechargeable battery and necessitate recharging every few days or weeks. Other relatively high-power consumption implantable devices, such as VADs and TAHs, may require power levels that an implantable rechargeable battery cannot supply for more than a few hours. With these devices, it may not be feasible to implant larger rechargeable batteries due to the size and space required. These devices necessitate recharging many times per day or the use of an external rechargeable battery pack.

A common issue encountered by powering or recharging high-power consumption implantable devices, such as VADs or TAHs, is the need for a percutaneous wire that exits the skin to transmit power from an external power source to an implanted battery or directly to the implanted device. This percutaneous wire can be a source of infection, restricts the patient from normal bathing or swimming, and can potentially leave the implanted device without power if it mechanically breaks. Some wireless power transfer systems have been developed that use inductive coupling between an implanted coil and an external coil to transfer power across the skin, thereby obviating the need for a percutaneous wire. This type of wireless power transfer system simply uses the inductive effect between two coils similar to a standard transformer. This approach has been used widely to recharge implanted batteries in some neural stimulators. However, these systems may require precise alignment between the two coils, require close spacing between coils on the order of a few inches or less, can generate significant amounts of heat near the skin, and require the patient to be immobile during charging if the external power source is not easily mobile.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

The discussion herein provides a description of a mobile wireless power transfer system intended to recharge implantable batteries, power implantable medical devices, or simultaneously power active implantable medical devices while recharging implantable batteries. The system so described may be worn by the patient during normal daily activities.

In an illustrative implementation, a mobile wireless power transfer system for implantable medical devices includes a mobile wireless power source and an implanted receiving assembly. The mobile wireless power source includes an excitation coil and transmitting resonant coil which are inductively coupled to each other and are housed in a durable housing. The durable housing also contains a rechargeable battery pack, an RF amplifier, and electronics required to control the amount of transmitted power. The receiving assembly includes a receiving resonant coil and a power pick-up coil which are also inductively coupled to each other. In some implementations, receiving assembly may be housed in a hermetically-sealed biocompatible housing that can be implanted in a human body. The transmitting and receiving resonant coils are constructed as to have closely matched or identical resonant frequencies so that the magnetic field produced by the transmitting resonant coil causes the receiving resonant coil to resonate strongly. The receiving resonant coil may resonate even when the distance between the two resonant coils greatly exceeds the greatest dimension (e.g. largest of the length, width, diameter, etc.) of either coil or the two resonant coils are largely misaligned axially (not concentric) or angularly (not parallel). In this way, the transmitting and receiving resonant coils are coupled by magnetic resonance. The power pick-up coil inductively receives energy from the magnetic field of the receiving resonant coil to provide power to an implantable medical device.

An apparatus of the present disclosure may be used in wireless energy transfer to power an implantable medical device. According to some embodiments, the apparatus comprises: a rechargeable power source configured to transmit electromagnetic energy, the power source comprising: a transmitting resonant coil having a first conductor; and an excitation coil configured to be inductively coupled to said transmitting resonant coil; a receiving assembly configured to be magnetic resonance coupled to the power source, the receiving assembly comprising: a receiving resonant coil having a second conductor; and a power pick-up coil configured to be inductively coupled to said receiving resonant coil.

According to some embodiments, the first or second conductor comprises an electrically conductive foil forming a coil structure, wherein an electrically insulative material is coupled to a surface of the foil, such that the insulative material and a layer of air, vacuum, or inert gas are provided between radially adjacent layers of the conductive foil. A rigidity of the insulative material exceeds a rigidity of the conductive foil. The excitation coil or power pick-up coil is within the enclosed volume of the respective resonant coil.

According to some embodiments, the power source is wearable by a patient. The power source comprises a battery. The power source comprises a radio frequency amplifier operable at a frequency between about 30 KHz and about 15 MHz.

According to some embodiments, the receiving assembly further comprises an implantable device configured to control the radio frequency amplifier through a wireless communication link between the implantable device and the wireless power source. The wireless communication link between the implantable device and the power source is configured to convey a control parameter comprising an indicia of an amount of power received by the implantable device from the wireless power source, wherein the radio frequency amplifier is configured to adjust an output based on the control parameter. The indicia may be proportional to an amount of power received by the implantable device from the wireless power source. The radio frequency amplifier can be configured to hold a constant output when the control parameter is not obtained from the wireless communication link between the implantable device and the power source. The radio frequency amplifier can be configured to reduce an output to zero when the control parameter is not obtained from the wireless communication link between the implantable device and the power source. An amount of electrical current drawn from the battery is an indicator of a coupling coefficient between the transmitting and receiving resonant coils. The power source further comprises a coupling display configured to display the indicator of the coupling coefficient.

According to some embodiments, the first conductor or second conductor provides a continuous electrically conductive layer arranged around all surfaces of a coil structure formed from an electrically non-conductive material. The receiving assembly is contained in a hermetically-sealed biocompatible housing, and the receiving assembly is implanted into a human body. The power pick-up coil is within the enclosed volume of the receiving resonant coil. The excitation coil is within the enclosed volume of the transmitting resonant coil. The first conductor or second conductor is insulated from previous or subsequent coil turns by one or more insulating media having a dielectric dissipation factor of 0.01 or less. The receiving assembly provides power to recharge an implantable battery, to operate an implantable medical device, or to simultaneously recharge an implantable battery and operate an implantable medical device.

According to some embodiments, the charge status of the power source battery or battery pack is displayed on the outside of the power source for patient viewing. An alarm signal generated by the implanted device is wirelessly received and displayed on the outside of the power source for patient viewing. An alarm signal generated by the implanted device is wirelessly received and indicated audibly by the power source for patient hearing. The receiving assembly contains a rectification circuit for converting high frequency AC power to DC power for use by an electronics module.

An apparatus of the present disclosure may be used in wireless energy transfer to power an implantable medical device. According to some embodiments, the apparatus comprises: a transmitting assembly configured to transmit electromagnetic energy, the transmitting assembly comprising: a transmitting resonant coil having a first conductor and a first insulating medium between coil turns of the first conductor; and an excitation coil configured to be inductively coupled to the transmitting resonant coil; and a radio frequency amplifier connected to the excitation coil; and a receiving assembly configured to be magnetic resonance coupled to the transmitting assembly, the receiving assembly comprises: a receiving resonant coil providing a second conductor and a second insulating medium between coil turns of the second conductor; and a power pick-up coil configured to be inductively coupled to the receiving resonant coil; and wherein the first or second insulating medium comprises a dielectric material that is solid.

According to some embodiments, the first or second insulating medium has a polygonal cross section. The dielectric material has a dielectric dissipation factor of 0.01 or less. One or more external capacitors are connected to a start and an end of the first conductor or second conductor, and the external capacitors have a temperature coefficient of less than 3000 ppm/degree C. and a total capacitance at least 90 percent of the total capacitance of the transmitting or receiving resonant coil. One or more external capacitors are connected to a start and an end of the first conductor or second conductor, and the one or more external capacitors have a dielectric dissipation factor of 0.01 or less. A largest dimension of the transmitting or receiving resonant coil is equal to or less than 3 inches. The transmitting or receiving resonant coil has a quality factor Q greater than 300.

A method of the present disclosure may be used in wireless energy transfer to power an implantable medical device. According to some embodiments, the method comprises: operating a radio frequency amplifier to generate electromagnetic energy in an excitation coil of a power source outside a patient; with the electromagnetic energy, inducing a first current in a transmitting resonant coil of the power source; with the first current, magnetic resonance coupling the transmitting resonant coil with a receiving resonant coil of a receiving assembly implanted within the patient; with the magnetic resonance coupling, inducing a second current in a power pickup coil of the receiving assembly; and with the second current, powering a device implanted within the patient.

According to some embodiments, the method further comprises controlling the radiofrequency amplifier with an implantable device through a wireless communication link between the implantable device and the wireless power source. According to some embodiments, the method further comprises, with the wireless communication link, conveying a control parameter comprising an indicia of an amount of power received by the implantable device from the wireless power source. According to some embodiments, the method further comprises, with the radio frequency amplifier, adjusting an output of the radio frequency amplifier based on the control parameter until the indicia is within a target range. According to some embodiments, the method further comprises holding a constant output of the radiofrequency amplifier when the control parameter is not obtained from the wireless communication link between the implantable device and the power source. According to some embodiments, the method further comprises reducing an output of the radiofrequency amplifier to zero when the control parameter is not obtained from the wireless communication link between the implantable device and the power source. According to some embodiments, the method further comprises displaying, on a coupling display of the power source, an indicator of a coupling coefficient between the transmitting and receiving resonant coils, wherein an amount of electrical current drawn from the battery is an indicator of the coupling coefficient.

A receiving assembly of the present disclosure may be implanted in the human body and used to wirelessly receive electromagnetic energy to power an implanted device. According to some embodiments, the receiving assembly comprises: a two piece housing fabricated from low dielectric loss ceramic material; and each ceramic housing piece incorporates a bonded metallic weld ring; and the metallic weld rings are joined by welding to create a hermetic barrier. A hermetic feedthru is welded to one or both metallic weld rings to provide a hermetic exit for electrically conducting lead wires. The receiving assembly is less than one inch thick. The receiving assembly may house or enclose a receiving resonant coil and/or a pick-up coil.

The foregoing has outlined rather broadly various features of the present disclosure in order that the detailed description that follows may be better understood. Additional features and advantages of the disclosure will be described hereinafter.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
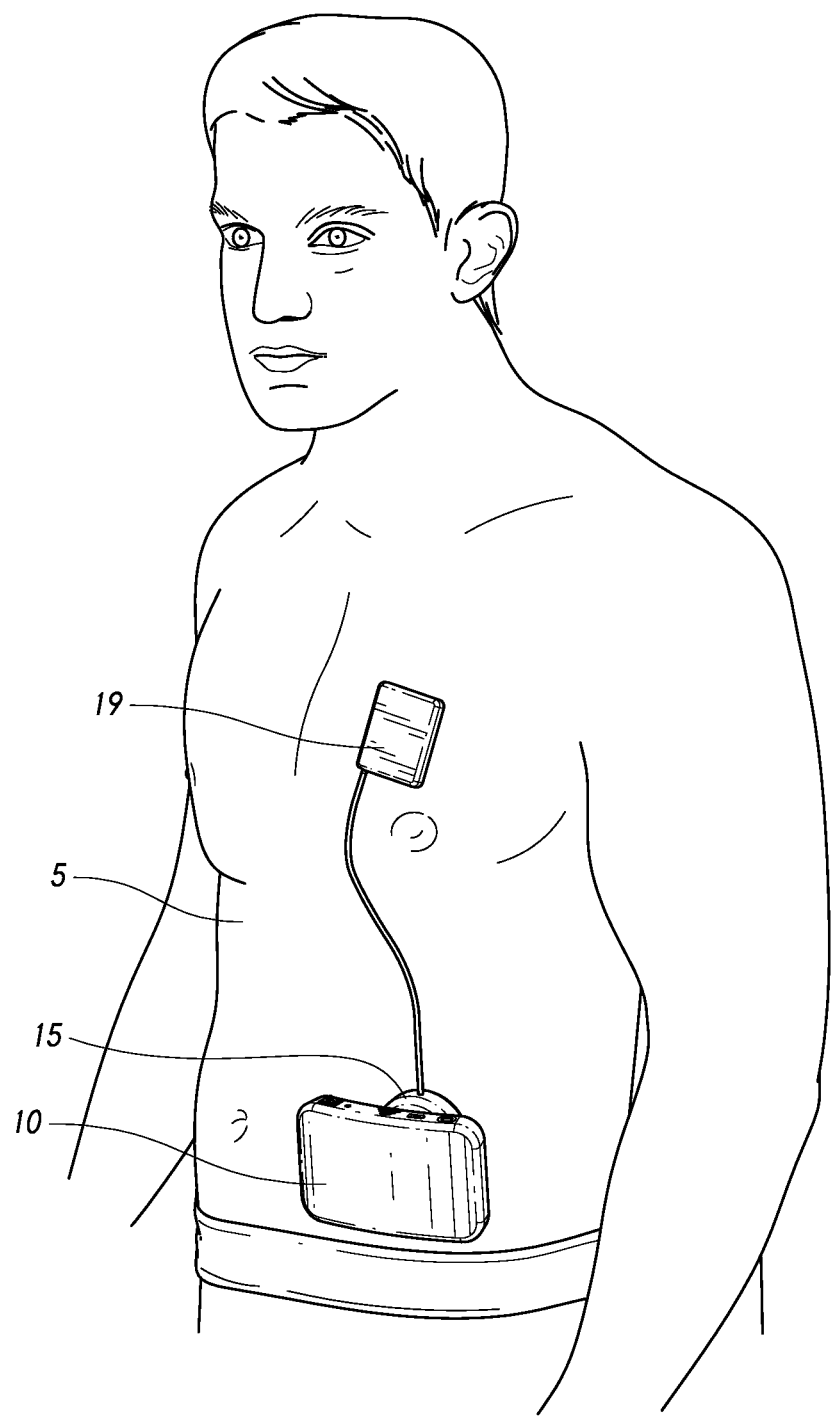
FIG. 1 shows a perspective view of a mobile wireless power system, in accordance with some embodiments of the present disclosure.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

This application incorporates by reference the entirety of U.S. Pub. No. 2012/0146575, published on Jun. 14, 2012; U.S. Pub. No. 2012/0150291, published on Jun. 14, 2012; and U.S. Pub. No. 2012/0089225, published on Apr. 12, 2012, each as if fully set forth herein.

Wide use of wireless power systems for various active implantable medical devices has not been adopted. Currently, few applications of wireless power transfer have been applied to VADs or TAHs due to the higher power transfer levels required, relatively high power consumption of such devices, limited space available for implantable rechargeable batteries, limited capacity of implantable rechargeable batteries, and the like. Mobile wireless power transfer systems and methods that can transfer sufficient power required to operate high-power consumption implantable devices while simultaneously recharging implantable batteries are discussed herein. These mobile wireless power transfer systems and methods eliminate percutaneous wires, provide sufficient power for operation and/or charging, provide improvement in the operation and/or charging range, allow the patient to live a more normal lifestyle, can be worn by patients, provide more patient mobility, and reduce skin heating effects.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The following detailed description provides implantable, energy efficient, small, mobile wireless power transfer systems and methods capable of providing power to an active implantable medical device and simultaneously recharging implantable batteries. The wireless power transfer systems and methods are capable of operating over extended distances between implanted receiving and external mobile transmitting coil assemblies, even when the receiving and transmitting coil assemblies are largely misaligned axially (not concentric) or angularly (not parallel). For example, the mobile wireless power systems and methods may be capable of transmitting power over distances up to several inches between resonant coils either axially, laterally, or axially and laterally separated. In some implementations, one or more components of the wireless power system may be implanted and the system may transmit power through the skin without percutaneous wires. In a non-limiting illustrative implementation of the mobile wireless power system and method, the mobile wireless power transfer system may be suitable for use with a ventricular assist device (VAD) or total artificial heart (TAH). The receiving coil assembly may be implanted in any suitable physical location in a patient's body including, but not limited to, abdominally or pectorally. Those skilled in the art will appreciate that the various features discussed below can be combined in various manners, in addition to the implementations discussed below. The illustrative implementations discussed herein are provided for illustrative purpose, and the scope of the invention is in no way limited to the specific illustrative implementations discussed herein.

Figure 2:
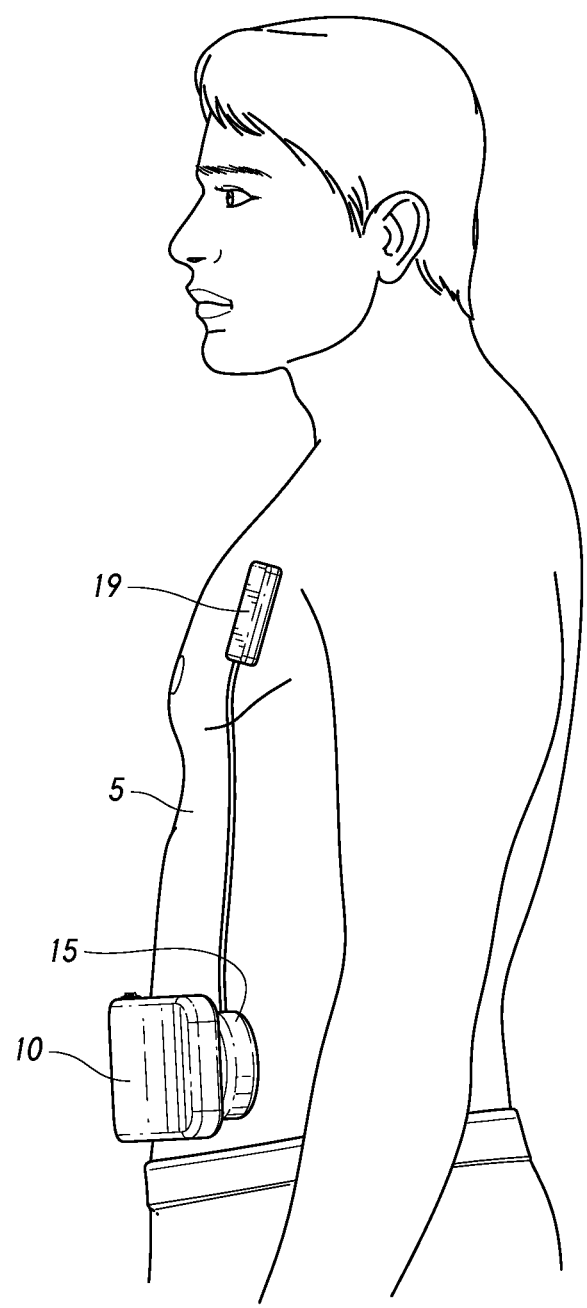
FIG. 2 shows a side view of a mobile wireless power system, in accordance with some embodiments of the present disclosure.
Figure 3:
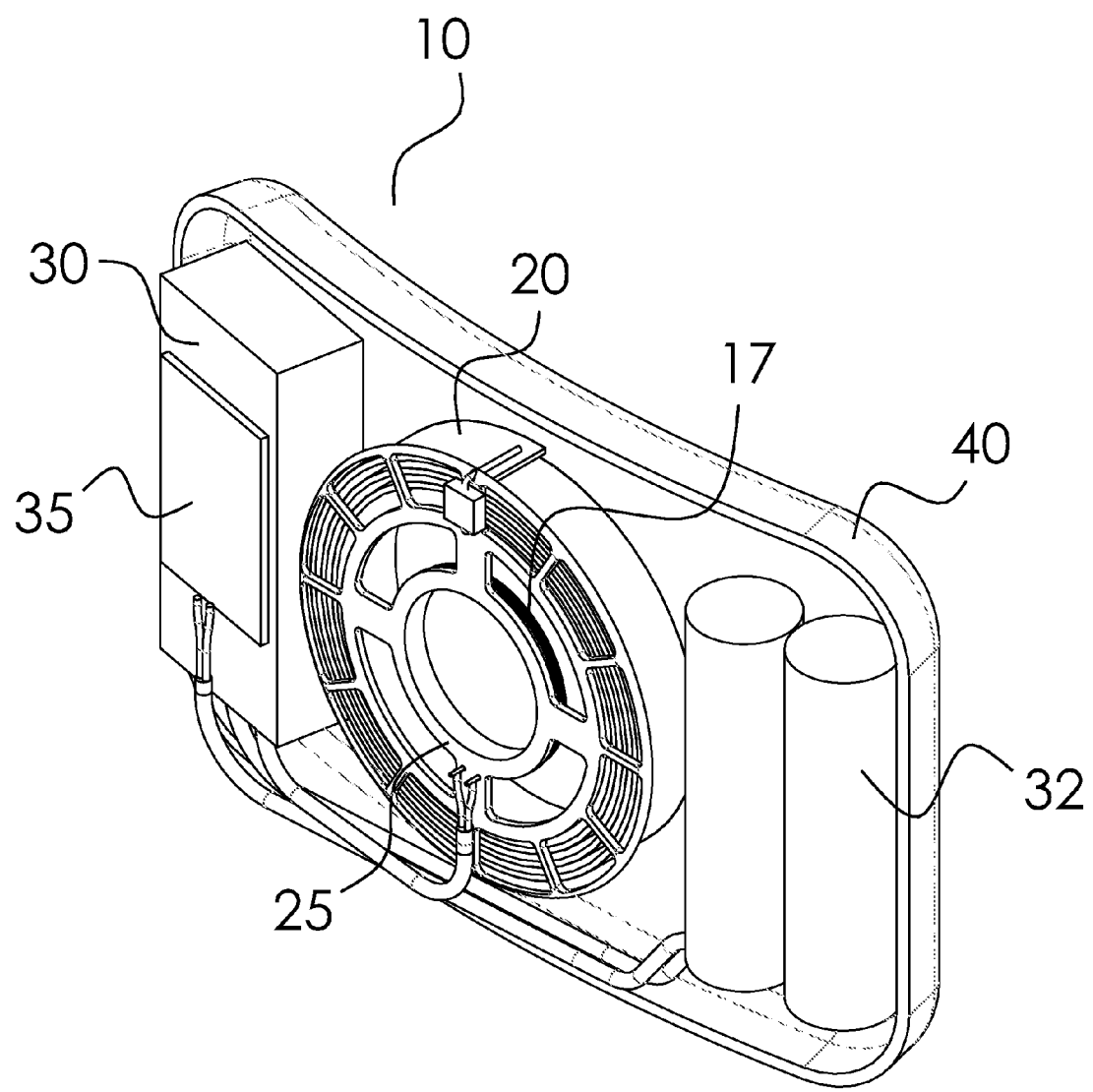
FIG. 3 shows an internal isometric view of a mobile wireless power source, in accordance with some embodiments of the present disclosure.
Figure 4:
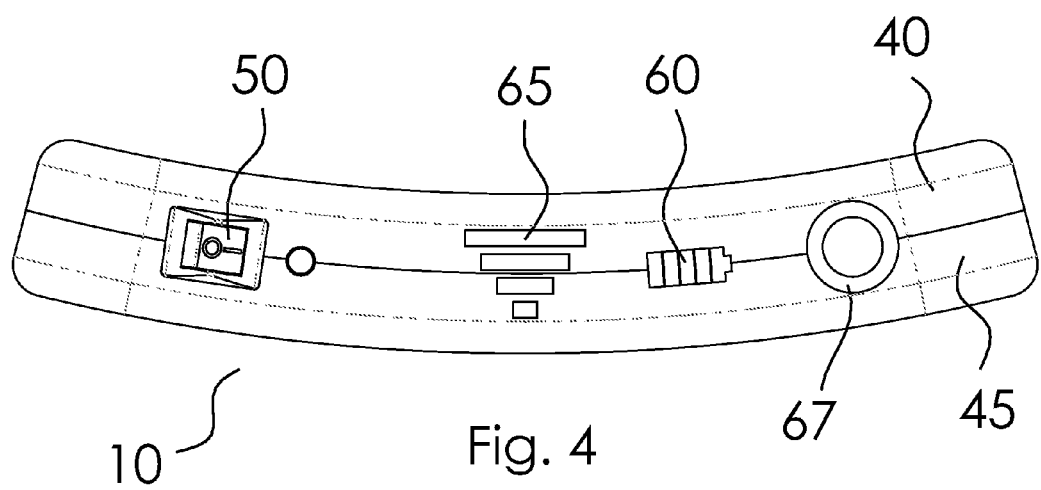
FIG. 4 shows a top view of a mobile wireless power source, in accordance with some embodiments of the present disclosure.
Figure 5:
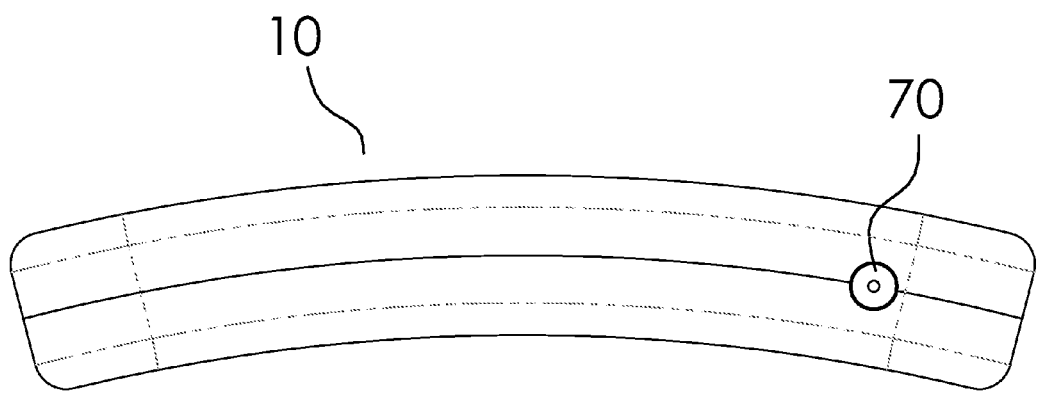
FIG. 5 shows a bottom view of a mobile wireless power source, in accordance with some embodiments of the present disclosure.
Figure 6:
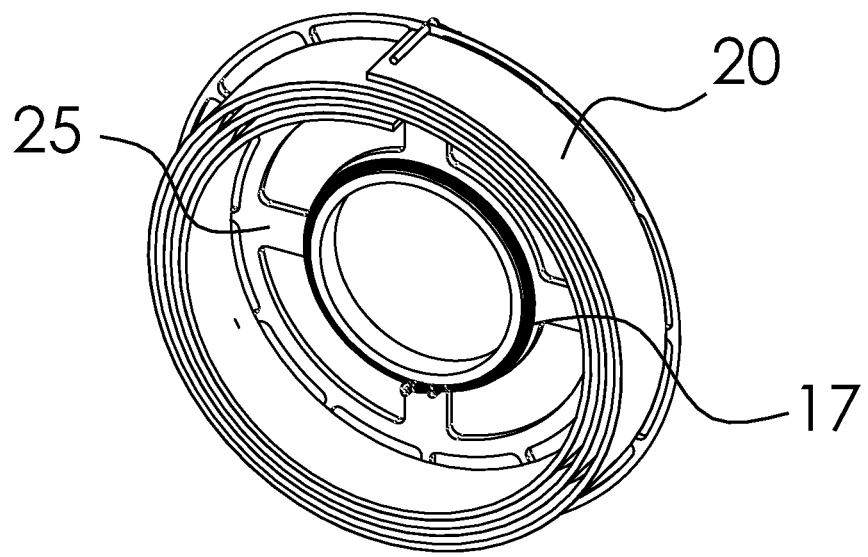
FIG. 6 shows a trimetric view of a transmitting coil assembly, in accordance with some embodiments of the present disclosure.

FIG. 1 and FIG. 2 are perspective and side views, respectively, of an illustrative implementation of a mobile wireless power system 5. Mobile power system 5 includes mobile power source 10, implanted receiving assembly 15, and active implanted device 19. Mobile wireless power source 10 may be worn in a garment such as a waistband, vest, or holster. FIG. 3 is an internal isometric view of mobile wireless power source 10 which may include an excitation coil 17, transmitting resonant coil 20, mounting frame 25, RF amplifier 30, battery pack 32, electronics module 35, and housing 40. FIG. 4 is a top view of assembled mobile wireless power source 10 that also includes switch 50, battery status indicator 60, coil coupling display 65, and master alarm indicator 67. FIG. 5 is a bottom view of assembled mobile wireless power source 10 that also includes DC power receptacle 70. FIG. 6 is a trimetric view of an illustrative implementation of a transmitting coil assembly showing excitation coil 17, transmitting resonant coil 20, and mounting frame 25. Excitation coil 17 is placed close enough to transmitting resonant coil 20 to be inductively coupled such that when high frequency AC power, such as that from RF amplifier 30, with a frequency of between about 30 KHz and about 15 MHz, is supplied to excitation coil 17, this causes transmitting resonant coil 20 to resonate resulting in a local time varying magnetic field.

Figure 7:
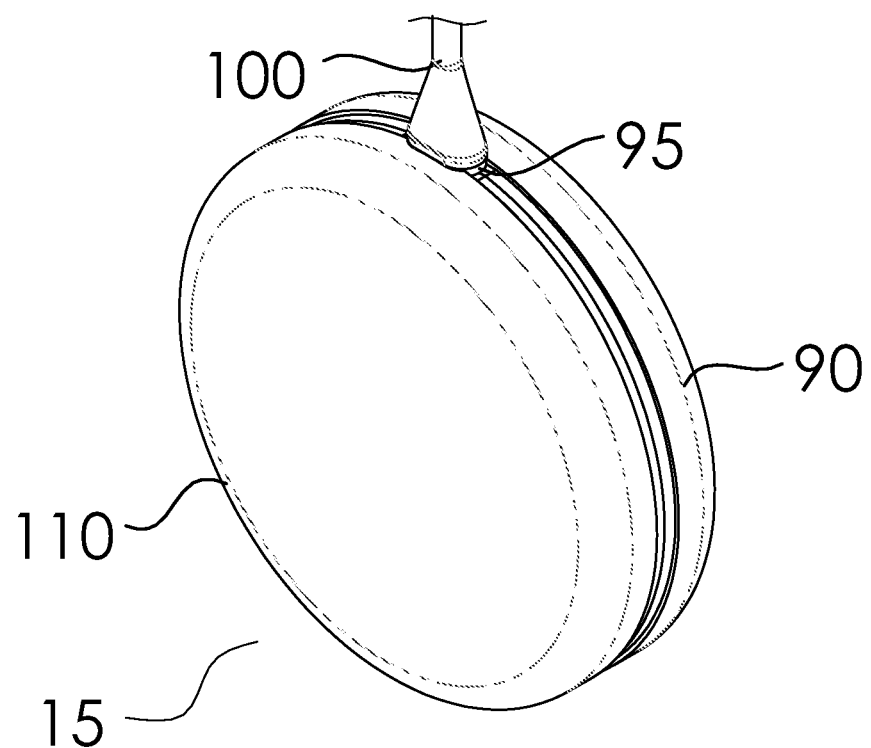
FIG. 7 shows an isometric view of a receiving assembly, in accordance with some embodiments of the present disclosure.
Figure 8:
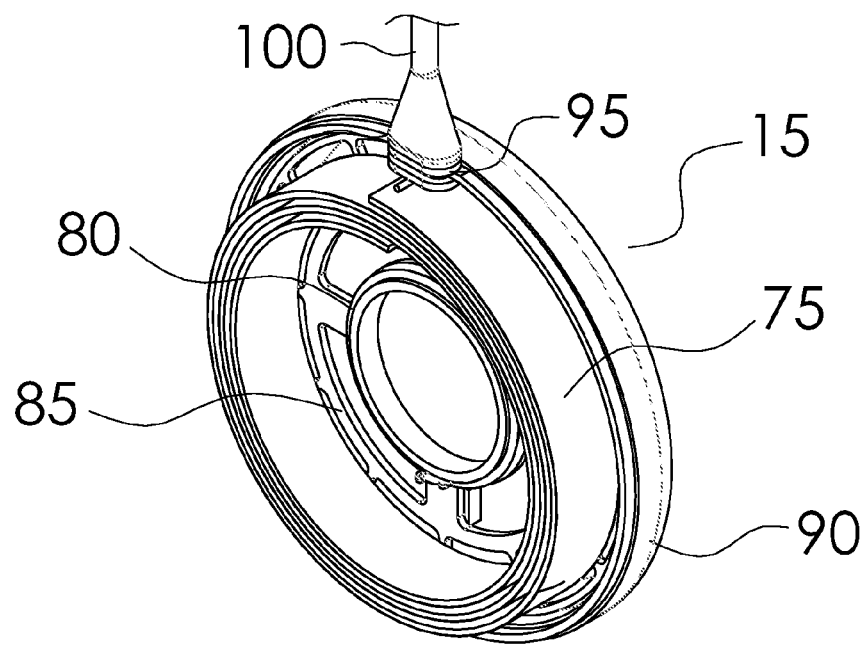
FIG. 8 shows an internal isometric front view of a receiving assembly, in accordance with some embodiments of the present disclosure.
Figure 9:
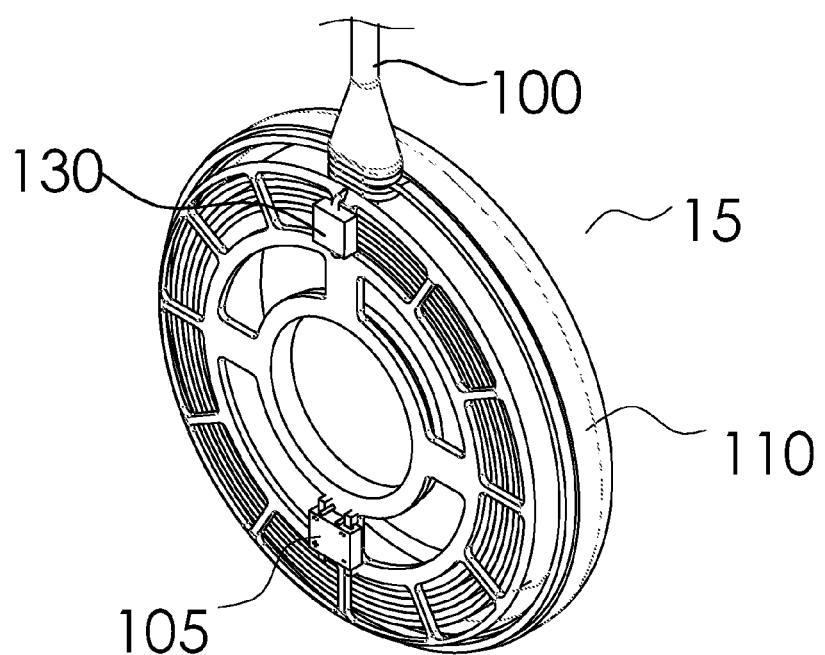
FIG. 9 shows an internal rear isometric view of a receiving assembly, in accordance with some embodiments of the present disclosure.

FIG. 7 is an isometric view of an illustrative implementation of receiving assembly 15 showing biocompatible housing 90, electrical feedthru 95, electrical lead 100, and cover 110. FIG. 8 is an internal isometric front view of an illustrative implementation of receiving assembly 15 showing receiving resonant coil 75, power pick-up coil 80, mounting frame 85, biocompatible housing 90, electrical feedthru 95, and electrical lead 100. FIG. 9 is an internal isometric rear view of receiving assembly 15 showing rectification circuitry 105, cover 110, and external capacitor 130.

The magnetic field produced by transmitting resonant coil 20 causes receiving resonant coil 75 to strongly resonate also, generating its own local time varying magnetic field, and thereby achieves magnetic resonance coupling between the transmitting and receiving resonant coils. Magnetic resonance coupling is a phenomenon in which two resonant objects tuned to the same or similar frequency electromagnetically exchange energy strongly but interact only weakly with other non-resonant objects. For example, magnetic resonance coupling may allow energy to be transferred wirelessly between two resonant coils over significant distances, whereas inductive coupling requires the two coils to be placed close to each other. As used herein, "magnetic resonance coupling" is a wireless connection for transferring power between two objects that have the same or similar resonant frequency, $\omega$. For example, the resonant frequency of transmitting resonant coil 20 and the resonant frequency of receiving resonant coil 75 may be the same, meaning that they vary within a defined range. A comparison between the resonant frequencies of the transmitting resonant coil 20 and the receiving resonant coil 75 may be expressed as a variance factor equal to the difference between the resonant frequency of transmitting resonant coil 20 and the resonant frequency of the receiving resonant coil 75, divided by the resonant frequency of transmitting resonant coil 20. According to embodiments, the variance factor may be less than 0.2%. For example, the variance factor may be less than 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, or 0.20%. As used herein, "magnetic resonance coupled" is a state in which two objects, having the same or similar resonant frequency, are capable of transferring power wirelessly from one object to the other at a resonant frequency.

In such a system, power may be transferred wirelessly and efficiently through this magnetic resonance coupling over a much greater distance than that of currently known traditional inductive coupling. Power pick-up coil 80 is placed close enough to receiving resonant coil 75 so as to receive energy from receiving resonant coil 75 inductively, causing an AC voltage across power pick-up coil 80. This AC voltage can then be rectified to a DC voltage by rectification circuitry 105 and used to power an electrical load such as an implantable medical device and/or recharge implantable batteries.

Figure 10:
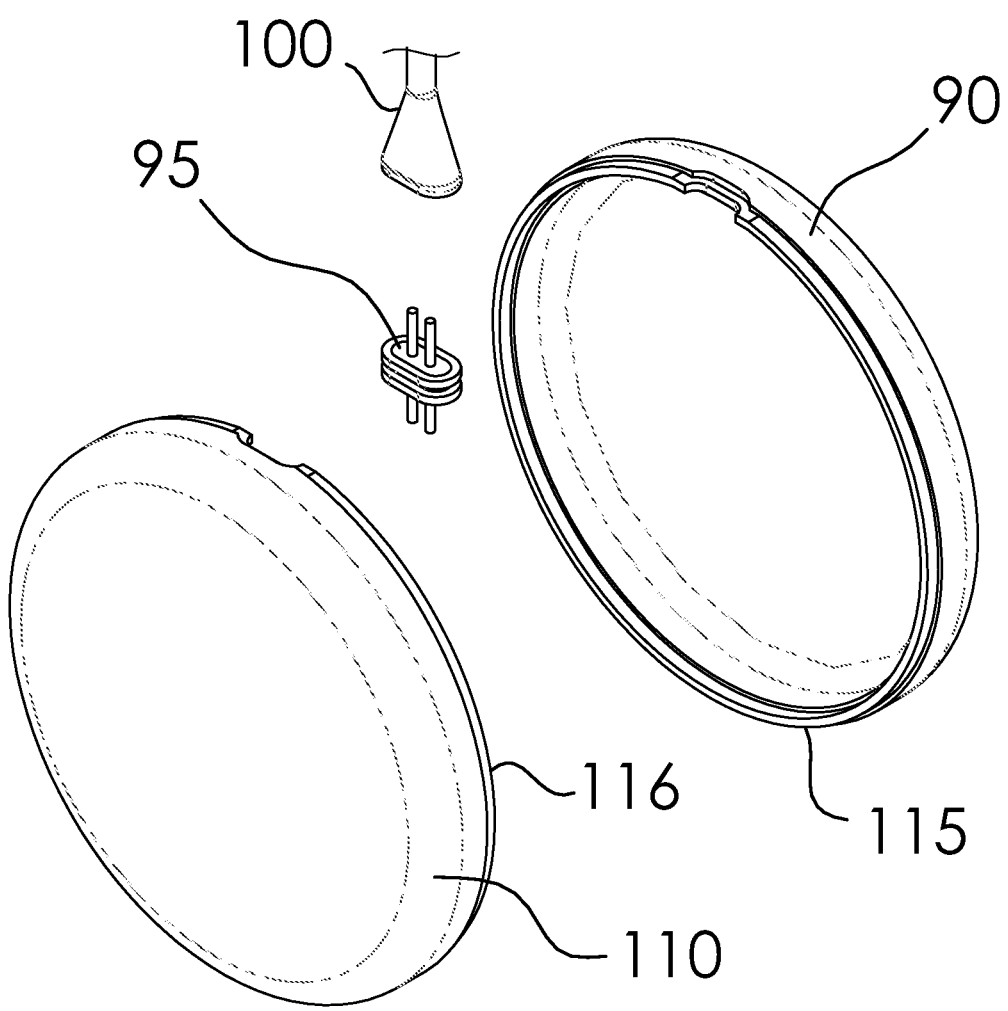
FIG. 10 shows a trimetric view of a receiving assembly showing weld rings, in accordance with some embodiments of the present disclosure.

Excitation coil 17 and power pick-up coil 80 may be made from a minimal number of conductor loops, and with any suitable conductor material, such as stranded or solid copper wire, so as not to produce too strong inductive coupling to their respective resonant coils 20 and 75 and thereby minimize the effect on resonant coil natural frequency and Q factor as discussed further below. Alternately, excitation coil 17 and power pick-up coil 80 may be made from a copper trace on a printed circuit board. Biocompatible housing 90 and cover 110 may be made from an RF transparent, low dielectric loss, hermetic, biocompatible material such as ceramics used in hermetic feedthru applications. Housing 90 and cover 110 incorporate titanium weld rings 115 and 116 as shown in FIG. 10 to provide a hermetic seal between housing 90, electrical feedthru 95, and cover 110. Titanium weld rings 115 and 116 may be joined by laser, electron beam, or any other suitable welding technique to form a hermetic seal.

Transmitting resonant coil 20 and receiving resonant coil 75 are designed to have closely matched or identical natural resonant frequencies as defined by equation 1.

$$\omega = \sqrt{\frac{1}{LC}} \quad [1]$$

where, ω=coil natural resonant frequency (radians/sec)
L=coil inductance (Henries)
C=coil capacitance (Farads)

The amount of energy that can be transferred to receiving resonant coil 75 is proportional to the strength of magnetic field emitted from transmitting resonant coil 20. The strength of the magnetic field emitted from transmitting resonant coil 20 should be maximized for a given amount of energy input to excitation coil 17 to optimize system efficiency and power transfer as well as minimize receiving assembly 15 size. This is accomplished by choosing a drive frequency F that is closely matched or identical to the natural resonant frequencies ω of transmitting 20 and receiving 75 resonant coils and by increasing resonant coil quality factor Q, given by equation 2:

$$Q = \sqrt{\frac{L}{C}} * \frac{1}{R} \quad [2]$$

where, Q=coil quality factor
L=coil inductance (Henries)
C=coil capacitance (Farads)
R=coil AC resistance (Ohms) at resonant frequency ω (radians/sec)

Each resonant coil should have a Q factor sufficiently high in order to provide reasonably efficient energy transfer.

Receiving assembly 15 may be implanted into a human body. Thus, it may be desirable to minimize the size of receiving resonant coil 75 and/or power pick-up coil 80 to be implanted. For example, the size of a receiving assembly 15 may be minimized by placing power pick-up coil 80 within the enclosed volume of receiving resonant coil 75. The outer diameter of power pick-up coil 80 can be made smaller than the inner diameter of receiving resonant coil 75, such that the natural resonant frequency and Q factor of receiving resonant coil 75 is minimally affected by power pick-up coil 80 when placed within the enclosed volume of receiving resonant coil 75. This provides an optimum state of system tuning for maximum power transfer and efficiency while minimizing receiving assembly 15 thickness and/or volume. It is important to achieve a receiving assembly 15 that is thin to allow for easy implantation and less noticeable implant site for patient comfort and well being. For example, in well tuned systems, receiving assembly 15 may be one inch or less in overall thickness. Transmitting resonant coil 20 and excitation coil 17 may be constructed in essentially the same manner.

As can be seen in equations 1 and 2, the factors affecting the coil quality factor Q are coil inductance, capacitance, AC resistance, and resonant frequency. Specifically, to maximize Q factor, the coil inductance and resonant frequency should be maximized while the coil capacitance and AC resistance should be minimized. However, as can be seen in equation 1, coil inductance and capacitance must be chosen correctly to achieve a desired coil natural resonant frequency. For the mobile wireless power transfer system disclosed herein, the desired coil resonant frequency is between about 30 KHz and about 15 MHz.

One method that can be utilized to increase coil inductance is to provide more coil turns at larger coil diameters. However, more coil turns and larger coil diameters require longer conductor lengths thereby increasing coil AC resistance and decreasing the benefit of higher inductance on coil Q factor. Additionally, more coil turns further increase coil AC resistance because of proximity effect. Proximity effect is a phenomenon in which the local magnetic fields of adjacent coil turns cause current flow to be constrained to smaller and smaller conductor areas as more coil turns are added. The net effect is that a decreasing portion of available conductor area is utilized as more coil turns are added. For example, the AC resistance of a coil with 4 turns can be several times higher than a coil of the same average diameter with only 2 turns, even if the conductor length of the 4 turn coil is only twice that of the 2 turn coil.

Another phenomenon that increases coil AC resistance relative to DC resistance is the skin effect. Skin effect is caused by the internal magnetic fields generated within a single turn of conductor, as opposed to proximity effect caused by multiple conductor turns. Skin effect is similar to proximity effect in that a decreasing portion of available conductor area is utilized as AC operating frequency is increased. This results in current flow that is more concentrated at the outer surfaces of a conductor as opposed to the interior portion of a conductor. The depth to which most of the current flow is constrained in a conductor operating at a given AC frequency is known as the skin depth and is given by equation 3:

$$\delta = \sqrt{\frac{2\rho}{f\mu}} \quad [4]$$

where, δ=skin depth (meters)
ρ=resistivity of conductor (Ohm-meters)
f=operating frequency (radians)
μ=absolute magnetic permeability of conductor (Henries/meter)

Therefore, it can be seen for a conductor of thickness T that is much thicker than the skin depth δ, most of the conductor is not utilized to pass AC current. The ratio of conductor thickness T to skin depth δ is known as the skin depth ratio. It is clear that increasing conductor thickness T above skin depth δ does little to reduce the AC resistance of a conductor, but merely increases coil volume and mass.

Notably, it is known in close coupled AC inductive transformer design that increasing conductor thickness T far above skin depth δ can worsen the proximity effect substantially, especially as more coil turns are added. For example, a high skin depth ratio above 2 can cause the AC resistance of an inductive transformer coil to be greater than 10 times higher than the same coil with a skin depth ratio of 1 or less, depending on the number of coil turns employed and operating frequency. Therefore, the conductor thickness T used in transmitting resonant coil 20 and receiving resonant coil 75 are chosen to produce a skin depth ratio of less than or equal to 2 to minimize proximity effects, reduce coil AC resistance, and increase coil quality factor Q. Similarly, a skin depth ratio less than one may be advantageous. In one implementation, copper or silver foil of a thickness less than 0.020 inches is used. Counter intuitively, thin copper foil produces less AC resistance than thick copper foil for some of the operating frequencies disclosed herein. By utilizing a thin conductor, it is believed that sufficiently high quality factor may be achieved for both transmit and receive resonant coils. In our experiments using thin copper foil, a transmitting or receiving resonant coil with a quality factor above 300 was achieved for a coil size 3 inches or less in diameter and 0.5 inches or less in width, which would result in a receiving assembly sufficiently small to implant and a mobile power source small enough to be worn and carried by a patient.

As shown in equation 1, once the inductance of transmitting resonant coil 20 or receiving resonant coil 75 is fixed, the proper capacitance must be present for the coil to resonate at a desired frequency ω. Coil capacitance can either be intrinsic, added in the form of a fixed or variable capacitor, or both intrinsic and added. Intrinsic capacitance is that which is formed by the coil geometry itself. For example, a coil with turns made from copper or silver foil separated by one or more insulating dielectric materials such as PTFE, low-loss PTFE, polyethylene, polypropylene, vacuum, an inert gas, air, or combinations thereof could be analogous to a flat plate capacitor of equal plate area and plate separation distance. However, intrinsic coil capacitance cannot be calculated in the same manner as a flat plate capacitor due to the effect of multiple turns. Many dielectric materials, such as those listed previously, are suitable to provide this intrinsic capacitance; however it is important that the materials have a low dielectric dissipation factor to not detrimentally impact the overall coil Q. To maintain an overall coil Q factor sufficiently high for adequate power transfer, the one or more insulating materials should have a dielectric dissipation factor of 0.01 or less at the coil resonant frequency.

It is desirable for transmitting resonant coil 20 and receiving resonant coil 75 to have as little intrinsic capacitance as possible. This is done to minimize the sensitivity of the resonant coils to extraneous objects via capacitive coupling which can shift their resonant frequencies and detune the system, resulting in lost power and efficiency.

Figure 11:
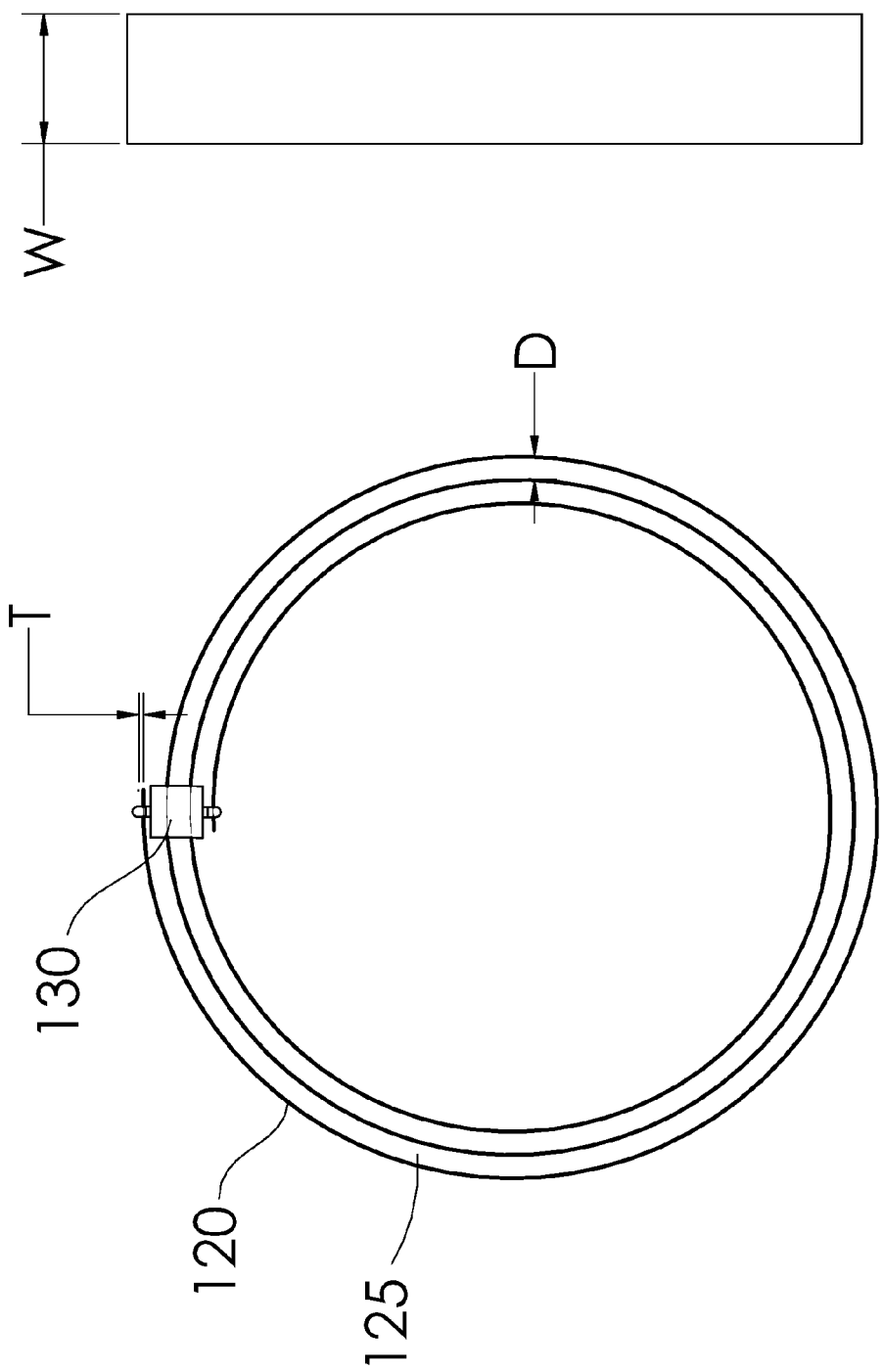
FIG. 11a shows a front view of a resonant coil, in accordance with some embodiments of the present disclosure.
FIG. 11b shows a side view of a resonant coil, in accordance with some embodiments of the present disclosure.

FIG. 11a and 11b show illustrative implementations of a resonant coil, such as a transmitting or receiving resonant coil, with single wrap conductive foil 120. In one implementation, resonant coils 20 and 75 achieve very low intrinsic capacitance using a flat conductor geometry, such as conductive foil 120 constructed from one or more high conductivity materials such as copper or silver, separated by an insulating medium 125 composed of one or more low dielectric constant materials such as PTFE, low-loss PTFE, polyethylene, polypropylene, vacuum, an inert gas, air, or any combination thereof with relatively large spacing D between turns as shown in FIG. 11a. For example, a solid insulative material may be provided on at least one side of a conductive foil 120, with a gap for receiving air, vacuum, or an inert gas to be provided between windings of the coil structure of the conductive foil 120. The rigidity of the solid material maintains the conductive foil 120 in its shape, while the air, vacuum, or inert gas of the gap minimizes dielectric losses between the windings. As described previously, the one or more insulating materials should have a dielectric dissipation factor of 0.01 or less at the coil resonant frequency to maintain an overall coil Q factor sufficiently high for adequate power transfer. Spacing D indicates the total thickness of the insulating medium 125. Spacing D may also include a gap for providing air, vacuum, or an inert gas. In some implementations, insulating medium 125 may be composed of at least one solid material that also provides mechanical support for the conductive foil 120. For example, the solid electrically insulating material may have a rigidity that is greater than a rigidity of the electrically conductive material used to form resonant coils 20 and/or 75. This enables the conductive foil 120 of resonant coils 20 and/or 75 to be desirably thin, rather than rely on its own structure to maintain its shape. This thinness reduces the impact of skin effect and proximity effect, while allowing resonant coils 20 and/or 75 to provide gaps of air, vacuum, or inert gas between windings of resonant coils 20 and/or 75. Such gaps reduce the intrinsic capacitance of the resonant coils 20 and/or 75, reduce the impact of proximity effect, and enhance the Q factor of the resonant coils 20 and/or 75. This configuration further facilitates these achievements while allowing the resonant coils 20 and/or 75 to be formed in a smaller volume than would be possible if other conductor shapes were utilized. This smaller volume enhances the capability of the receiving assembly 15 to be implanted within a patient. Smaller-sized devices are desirable for implant purposes. In some implementations, insulating medium 125 may be composed of at least one material with a polygonal cross section that also provides mechanical support for the conductive foil 120. A polygonal cross section, defined as a cross sectional shape with all straight sides, is chosen as it is a readily available form of PTFE, low loss PTFE, polyethylene, and polypropylene and results in a volume efficient resonant coil assembly. In the side view shown in FIG. 11b, width W may indicate the width of the conductive foil 120 and insulating medium 125. The amount of intrinsic capacitance can be varied by increasing/decreasing the spacing D between coil turns or increasing/decreasing the conductor width W. Spacing D can be kept constant or varied between any adjacent turns. One or more fixed or variable external capacitors 130 with low temperature sensitivity may be added across the start and end of the coil turns to tune the coil to a desired resonant frequency. Low dielectric dissipation factor external capacitors should be used so that when combined with the insulating medium 125, the combined dielectric dissipation factor of the external capacitor 130 and insulating medium 125 is low to maintain an overall coil Q factor sufficiently high for adequate power transfer. Low temperature sensitivity external capacitance with a temperature coefficient of less than 3000 ppm/degree C. should be used and the external capacitance should greatly exceed the intrinsic capacitance to positively impact the stability of the overall coil resonant frequency.

In an illustrative implementation, conductive foil 120 used in resonant coils 20 and 75 is chosen with a thickness T, such that the skin depth ratio is less than 2 for a given operating resonant frequency between 30 KHz-15 MHz. This is done to decrease the coil AC resistance and thereby increase coil Q factor. Conductive foil 120 may be adhered to the electrically non-conductive insulating medium 125 with any suitable adhesive such as epoxy, urethane, silicone, or acrylic.

Alternately, the conductive path of resonant coils 20 and 75 may be formed by electroplating or electroless plating of a conductive material such as copper or silver onto a suitable electrically non-conductive form. This may result in multiple advantages. First, manufacturing material and labor costs may be lower due to eliminating costs associated with adhering conductive foil to an electrically non-conductive form. Secondly, the conductive path formed by electroplating or electroless plating is continuous around the electrically non-conducting form which may further lower coil AC resistance and increase coil Q factor. The thickness of the conductive layer plated onto the electrically non-conductive form is chosen such that the skin depth ratio is less than 2 for a given operating frequency between 30 KHz-15 MHz. Again, this is done to minimize the proximity effect and lower coil AC resistance and increase coil Q factor. Electroless plating of conductive material onto an electrically non-conductive form may be preferred over electroplating to produce a more uniform conductor thickness throughout the coil geometry. The electrically non-conductive form may be made from a material that is readily platable with copper or silver such as ABS, nylon, or polycarbonate.

Another factor which determines how much power can be transferred between transmitting resonant coil 20 and receiving resonant coil 75 is the coupling coefficient between coils. The coupling coefficient is a function of coil geometry and relative spacing between coils and varies between 0 and 1. Higher coupling coefficients allow more power to be transferred between resonant coils for the same input power or the same power transferred between resonant coils using less input power. Regulating power transfer is important to charge an implanted battery and/or energize an implanted device. Varying coupling coefficients due to position changes of mobile power source 10 can cause inadequate or excess power to be transferred for a given input power.

Figure 12:
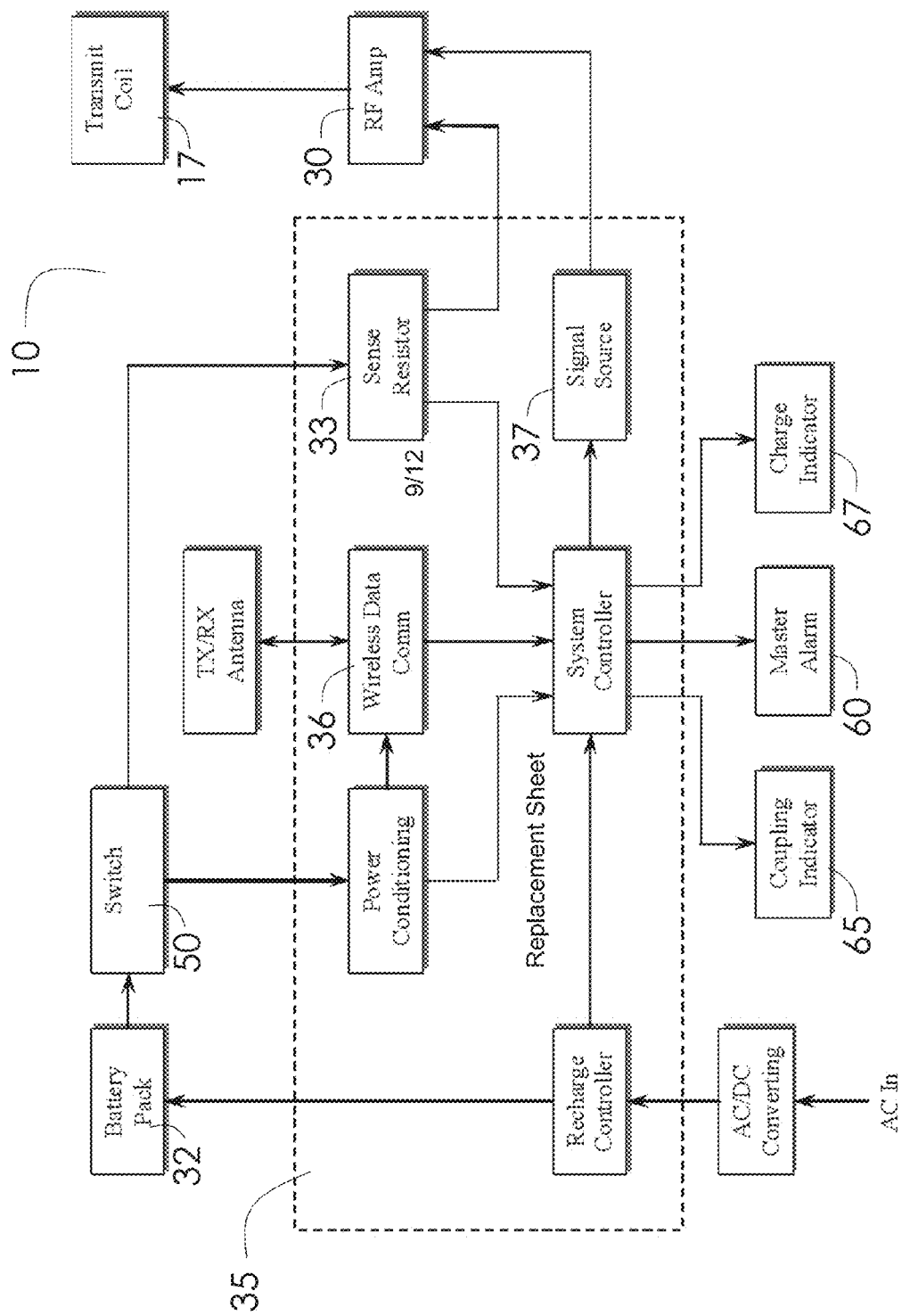
FIG. 12 shows a functional block diagram of electronics controlling a wireless mobile power source, in accordance with some embodiments of the present disclosure.

FIG. 12 is a functional block diagram of electronics module 35. Electronics module 35 contains communication and power regulating circuitry to control the amount of power transferred to receiving assembly 15.

Figure 13:
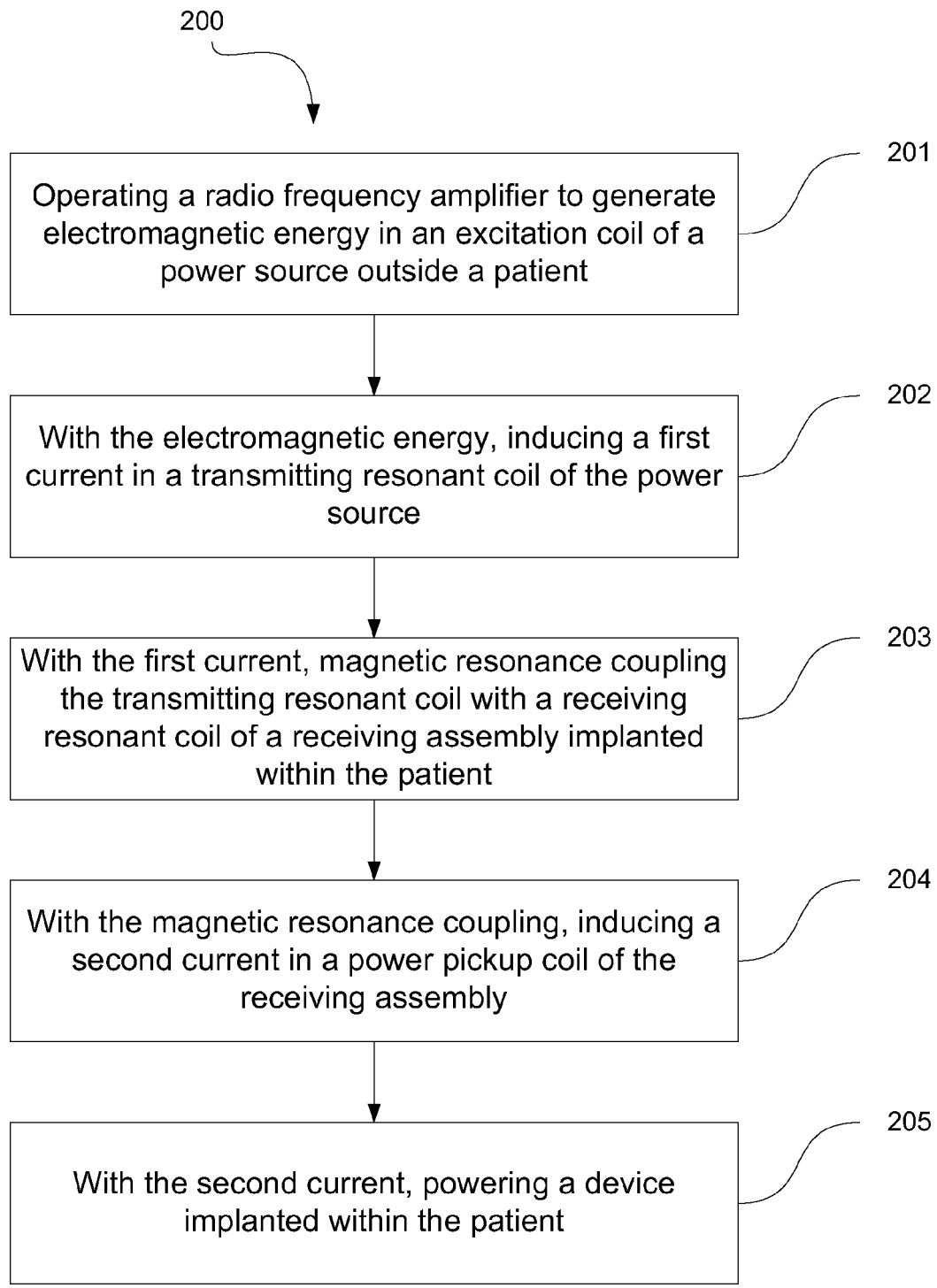
FIG. 13 shows a flow chart of a method of operating components of a wireless power system, in accordance with some embodiments of the present disclosure.

FIG. 13 shows a flow diagram of an exemplary method 200 of operation. With reference to FIG. 13, the method 200 includes a step 201 for operating a RF amplifier 30 to generate electromagnetic energy in an excitation coil 17 of a power source 10 outside a patient. In step 202, the electromagnetic energy induces a first current in a transmitting resonant coil 20 of the power source 10. In step 203, the first current transfers power via a magnetic resonance coupling between the transmitting resonant coil 20 and a receiving resonant coil 75 of a receiving assembly 15 implanted within the patient. In step 204, the magnetic resonance coupling induces a second current in a power pickup coil 80 of the receiving assembly 15. In step 205, the second current powers a device implanted within the patient.

Figure 14:
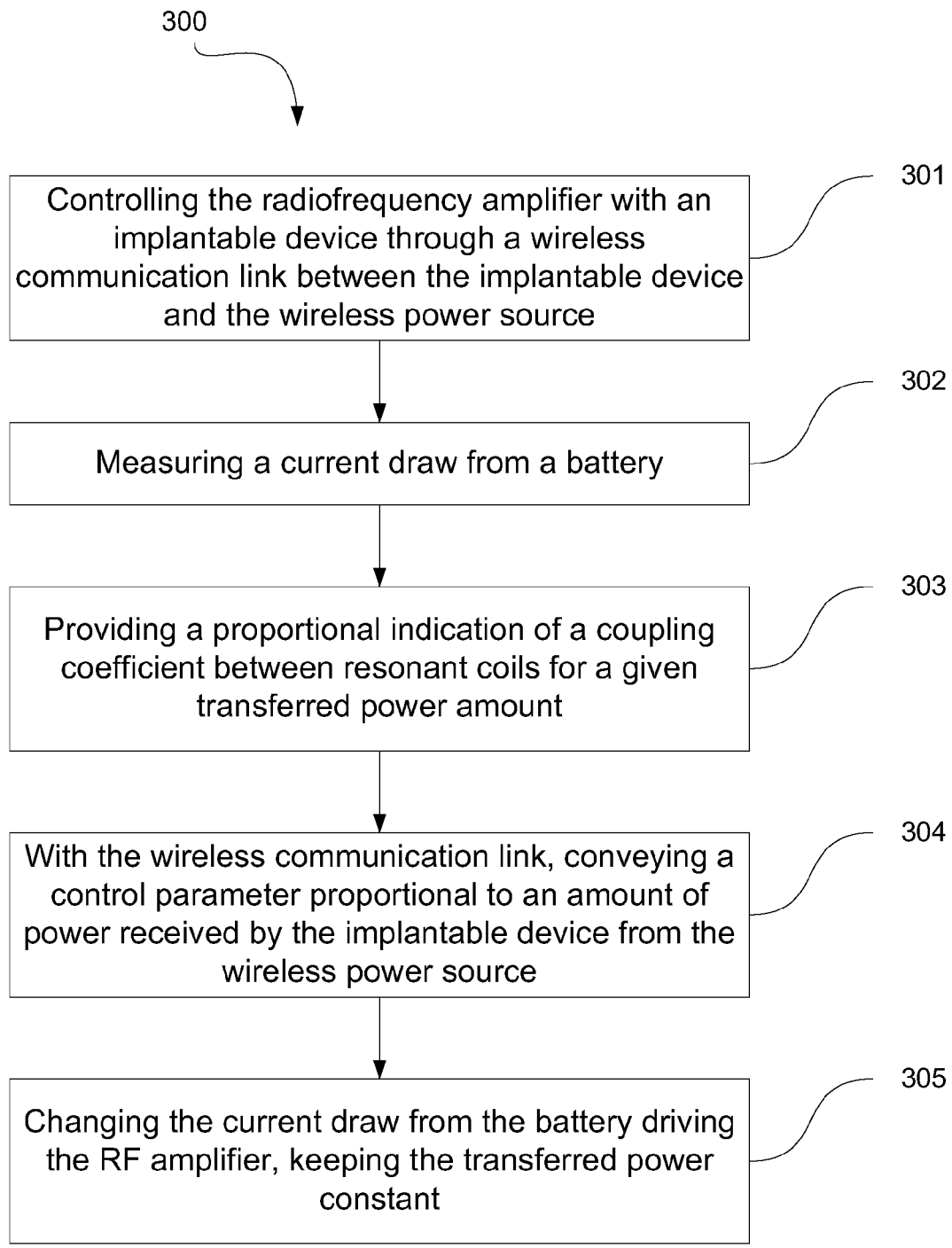
FIG. 14 shows a flow chart of a method of operating components of a wireless power system, in accordance with some embodiments of the present disclosure.

FIG. 14 shows a flow diagram of an exemplary method 300 of operation. With reference to FIGS. 12 and 14, electronics module 35 incorporates wireless communication module 36 to enable data exchange between implanted device 19 and mobile power source 10. As components are controlled, as shown in step 301, the data exchange includes parameters indicating the amount of power being received by receiving assembly 15, as shown in step 302. Electronics module 35 also contains a variable amplitude signal source 37 for driving RF amplifier 30. In doing so, electronics module 35 may regulate the output power of RF amplifier 30 according to the wireless received power signal from implanted device 19 to keep the received power relatively constant as the coupling coefficient between transmit and receive resonant coils changes due to relative position changes between resonant coils. Electronics module 35 contains a control algorithm to maintain the received power by implanted device 19 constant within acceptable bounds by varying the output power of RF amplifier 30. Moreover, sense resistor 33 measures the current draw from battery pack 32, as shown in step 302, supplying power to RF amplifier 30 and can be used to provide proportional indication of the coupling coefficient between resonant coils for a given transferred power amount, as shown in steps 303 and 304. As the coupling coefficient between resonant coils changes, the current draw from battery pack 32 driving RF amplifier 30 will change due to the control function of electronics module 35 keeping the transferred power constant, as shown in step 305. The change in current draw from battery pack 32 is measured by sense resistor 33 and can be used to indicate relative coupling coefficient between resonant coils and displayed on coupling display 65. The charge status of battery pack 32 may be displayed on battery status indicator 60. Implanted device 19 may generate an alarm signal which can be received by wireless communication module 36 and displayed on master alarm 67.

Figure 15:
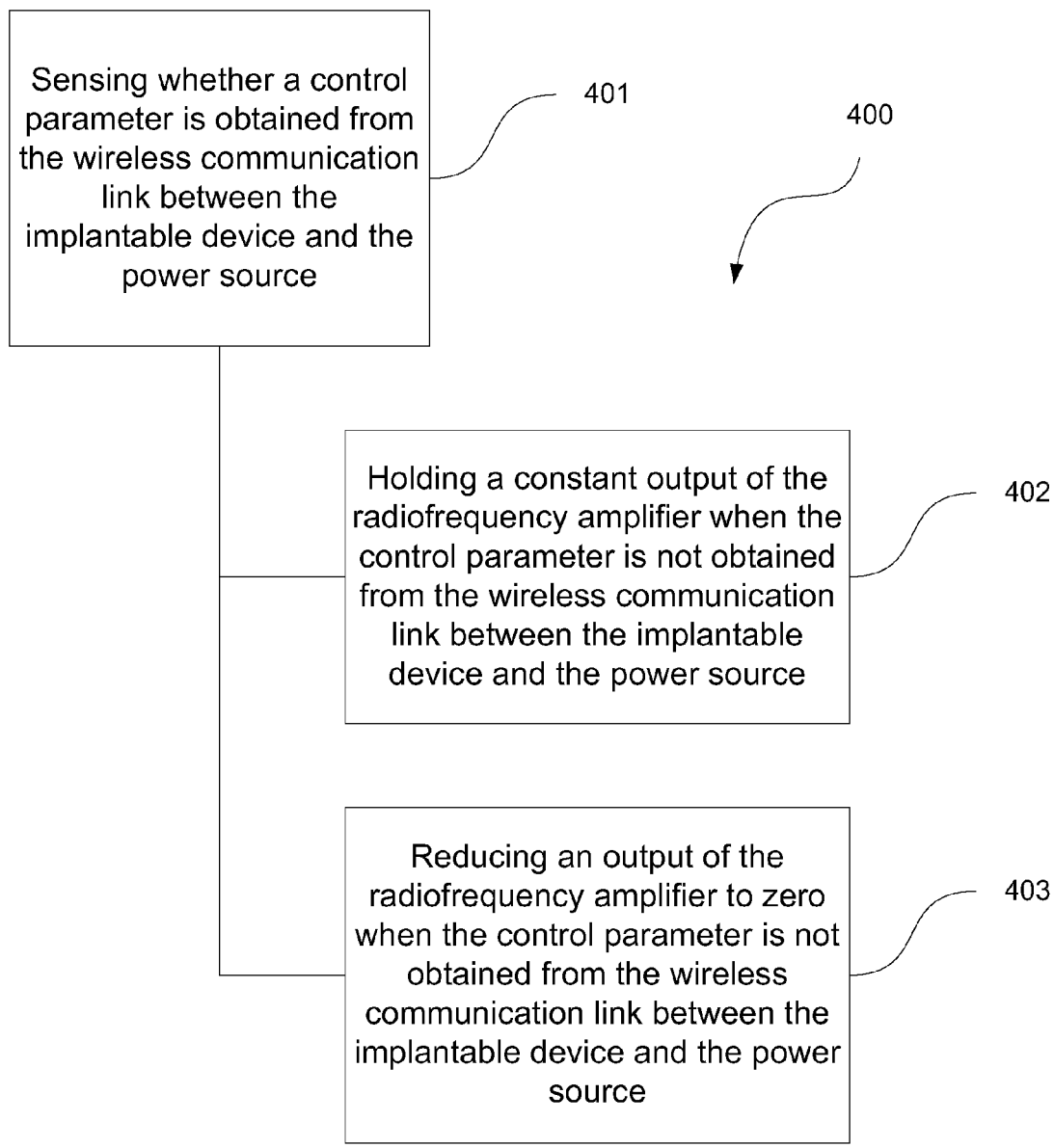
FIG. 15 shows a flow chart of a method of operating components of a wireless power system, in accordance with some embodiments of the present disclosure.

FIG. 15 shows a flow diagram of an exemplary method 400 of operation. Data exchange between implanted device 19 and mobile power source 10 indicating transferred power should be constant to prevent excessive or inadequate power transfer. This can account for potential rapid changes in coupling coefficient due to movement and migration of mobile power source 10 or reduced power demand when a rechargeable battery contained within implanted device 19 is fully charged. However, implanted device 19 may be required to communicate wirelessly with other external devices such as a patient monitor. The wireless communication protocol used by implanted device 19 may only allow for communication with one device at a time. Hence, mobile power source 10 may experience brief periods during operation without expected communication from implanted device 19. During such brief periods, electronics module 35 of mobile power source 10 may sense whether a control parameter is obtained from the wireless communication link between the implantable device and the power source (step 401) and hold the output power of RF amplifier 30 constant (step 402) or reduce to zero (step 403) until communication with implanted device 19 is subsequently received. As used herein, "wireless communication link" is a state between two components, in which the two components are capable of communicating wirelessly in at least one direction. The wireless communication link between mobile power source 10 and implanted device 19 may be a signal separate from other signals, such as those generated by excitation coil 17, transmitting resonant coil 20, receiving resonant coil 75, or power pick-up coil 80. The wireless communication link between mobile power source 10 and implanted device 19 may be a signal separate from signals communicated between mobile power source 10 and other objects, or between implanted device 19 and other objects.

The resonant coil implementation previously described is a right circular spiral coil. In other implementations, any suitable coil arrangement may be utilized, such as a rectangular coil, a helical coil, a square coil, or any other suitable structure. The number of turns may be one or more. The coil may be composed of a solid conductor, hollow conductor, flat conductor, Litz wire, any other suitable conductors, and/or a combination thereof. All manner of coil shapes, including, but not limited to, circles, squares, rectangles, octagons, other polygons, regular areas and irregular areas, are within the scope of this invention.

The mobile wireless power systems and methods described herein are implantable, energy efficient, small, and portable. The systems and methods are capable of providing power to an active implantable medical device and simultaneously recharging implantable batteries while being worn by a patient.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC.

It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

Components of devices disclosed herein may be configured to facilitate communication. Components may be configured to perform any type of wired or wireless communication. For example, components may send and receive radio frequency (RF) signals, infrared (IR) frequency signals, or other electromagnetic signals. Any of a variety of modulation techniques may be used to modulate data on a respective electromagnetic carrier wave. Communications protocols for managing communication between components are known, and may include IEEE 802.11, IEEE 802.3, Bluetooth, or Medical Implantable Communication Standard (MICS), etc.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. An apparatus for use in wireless energy transfer to power an implantable medical device, the apparatus comprising:
   a rechargeable power source configured to transmit electromagnetic energy, the power source comprising:
      a transmitting resonant coil;
      a radio frequency amplifier;
      a battery; and
      a first housing enclosing the transmitting resonant coil, the radio frequency amplifier, and the battery; and
   a receiving assembly configured to be magnetic resonance coupled to the power source, the receiving assembly comprising:
      a receiving resonant coil;
      a second housing and a cover, wherein the second housing and the cover each comprises a ceramic portion and a metallic ring, wherein the metallic rings are welded to each other; and
      an electrical feedthru providing an electrical connection from an interior of the second housing and cover to an exterior of the second housing and cover;
      wherein the second housing, the cover, and the electrical feedthru form a hermetic barrier enclosing the receiving resonant coil within the interior of the second housing and cover.

2. The apparatus of claim 1, wherein the power source is wearable by a patient.

3. The apparatus of claim 1, wherein the radio frequency amplifier is operable at a frequency between about 30 KHz and about 15 MHz.

4. The apparatus of claim 1, wherein the power source further comprises a coupling display configured to display an indicator of a coupling coefficient between the transmitting resonant coil and the receiving resonant coil.

5. The apparatus of claim 1, wherein each metallic ring is bonded to one of the ceramic portions.

6. The apparatus of claim 1, wherein the electrical feedthru is welded to one of the metallic rings.

7. The apparatus of claim 1, wherein the electrical feedthru is welded to both of the metallic rings.

8. The apparatus of claim 1, wherein the receiving assembly is less than one inch thick.

9. The apparatus of claim 1, wherein the metallic rings comprise titanium.

10. The apparatus of claim 1, wherein the electrical feedthru is connectable to an electrical lead.

11. The apparatus of claim 1, wherein the receiving assembly further comprises a rectification circuit enclosed by the hermetic barrier.

12. The apparatus of claim 1, wherein the receiving assembly further comprises an external capacitor enclosed by the hermetic barrier and connected to the receiving resonant coil.

13. The apparatus of claim 1, wherein the receiving assembly further comprises a power pick-up coil enclosed by the hermetic barrier and configured to be inductively coupled to said receiving resonant coil.

14. The apparatus of claim 1, wherein the rechargeable power source further comprises an excitation coil enclosed by the first housing and configured to be inductively coupled to said transmitting resonant coil.

* * * * *